United States Patent [19]

Teetz et al.

[11] Patent Number: 4,459,225
[45] Date of Patent: Jul. 10, 1984

[54] PEPTIDE AMIDES AND PROCESS FOR THEIR MANUFACTURE

[75] Inventors: Volker Teetz, Hofheim am Taunus; Rolf Geiger, Frankfurt am Main; Hans G. Alpermann, Königstein; Martin Bickel, Frankfurt am Main, all of Fed. Rep. of Germany

[73] Assignee: Hoechst Aktiengesellschaft, Frankfurt am Main, Fed. Rep. of Germany

[21] Appl. No.: 359,242

[22] Filed: Mar. 18, 1982

Related U.S. Application Data

[63] Continuation of Ser. No. 179,746, Aug. 20, 1980, abandoned.

[30] Foreign Application Priority Data

Aug. 22, 1979 [DE] Fed. Rep. of Germany ....... 2933947

[51] Int. Cl.³ ........................................... C07C 103/52
[52] U.S. Cl. ............................................. 260/112.5 R
[58] Field of Search ................... 424/177; 260/112.5 R

[56] References Cited

U.S. PATENT DOCUMENTS

| | | | |
|---|---|---|---|
| 2,820,781 | 1/1958 | Stevens | 424/112.5 R |
| 3,035,041 | 5/1962 | Schwyzer et al. | 424/112.5 R |
| 3,171,831 | 3/1965 | Town | 424/177 |
| 4,127,534 | 11/1978 | Coy et al. | 424/177 |
| 4,283,330 | 8/1981 | Shuman | 424/177 |

FOREIGN PATENT DOCUMENTS

| | | |
|---|---|---|
| 5248 | 11/1979 | European Pat. Off. |
| 2741393 | 9/1977 | Fed. Rep. of Germany |
| 2715803 | 10/1977 | Fed. Rep. of Germany |
| 2732451 | 2/1978 | Fed. Rep. of Germany |
| 2739440 | 3/1978 | Fed. Rep. of Germany |
| 2933947 | 12/1981 | Fed. Rep. of Germany |
| WO80/22 | 1/1980 | PCT Int'l Appl. |
| 1523812 | 9/1978 | United Kingdom |
| 1577115 | 10/1980 | United Kingdom |
| 1592385 | 7/1981 | United Kingdom |

OTHER PUBLICATIONS

Miller et al., "Distribution and Pharmacology of the Enkaphalins, etc.", pp. 195–213, London, 1978.
Robert George, et al., *Annual Review of Pharmacology and Toxicology*, XX, Calif., Annual Review Inc. 1980, pp. 61–110.
George R. Pettit, *Synthetic Peptides*, vol. 1, New York, Van Nostrand Reinhold Co., 1970, p. 5.

*Primary Examiner*—Delbert R. Phillips
*Assistant Examiner*—F. T. Moezie
*Attorney, Agent, or Firm*—Curtis, Morris & Safford

[57] ABSTRACT

New peptide amides of the formula I $$H-Tyr-D-Lys(For)-Gly-X \qquad (I)$$

wherein
For is formyl,
X is alkylamino, dehydro-Phe or Phe-alkylamido having up to 6 carbon atoms in the alkyl moiety, which moiety may be substituted by hydroxy and/or phenyl, Phe-cycloalkylamide or Phe-cycloalkylene amide having up to 8 carbon atoms in the cycloalkyl or cyclalkylene moiety, 1 to 2 $CH_2$ groups being optionally replaced by —NH—, —O—, —S— or —CO—, Phe-alkylene-cycloalkylamide having from 5 to 6 ring carbon atoms, which amide may be substituted by carbonamido, N-alkylcarbonamido or alkyl and 1 carbon atom whereof may be replaced by nitrogen, Phe-endo- or exo-norbornylamide or Phe-thiazolamide or Phe-thiazolidine-carboxylic acid amide, which may be substituted by 1 to 4 methyl groups each,
and process for their manufacture are disclosed. These peptide amides are distinguished by an analgetic activity and suppress the motility of the ileum of the guinea pig.

2 Claims, No Drawings

PEPTIDE AMIDES AND PROCESS FOR THEIR MANUFACTURE

This is a continuation, of application Ser. No. 179,746, filed Aug. 20, 1980 now abandoned.

The present invention relates to peptide amides of the formula I

H—Tyr—D—Lys(For)—Gly—X  (I)

wherein
For is formyl,
X is alkylamino, dehydro-Phe or Phe-alkylamido having up to 6 carbon atoms in the alkyl moiety, which moiety may be substituted by hydroxy and/or phenyl, Phe cycloalkylamide or Phe-cycloalkylene amide having up to 8 carbon atoms in the cycloalkyl or cyclalkylene moiety, 1 to 2-CH₂ groups being optionally replaced by —NH—, —O—, —S— or —CO—, Phe-alkylenecycloalkylamide having from 5 to 6 ring carbon atoms, which amide may be substituted by carbonamido, N-alkylcarbonamido or alkyl and 1 carbon atom whereof may be replaced by nitrogen, Phe-endo- or exo-norbornylamide or Phe-thiazolamide or Phe-thiazolidine-carboxylic acid amide, which may be sustituted by 1 to 4 methyl groups each.

The present invention furthermore relates to a process for the manufacture of the compounds of the formula I, which comprises condensing a peptide derivative of the formula II Y—Tyr—D—Lys(For)—Gly—OH  (II)

wherein Y is a protective group, preferably benzyloxycarbonyl or tertiary butyloxycarbonyl, with an amine XH or reacting a peptide derivative of the formula III Y—Tyr—D—Lys(For)—Gly—Phe—OH  (III)

with an amine XH, which does not contain the terminal phenylalanine radical (Phe) and subsequently splitting off the protective group Y.

The compounds according to the present invention can be synthesized according to the commonly known methods of peptide chemistry (cf. Houben-Weyl, Methoden der Organischen Chemie, vol. 15). The method involving the use of active esters particularly with addition of 1-hydroxybenzotriazole as the catalyst is preferred (cf. Chem.Ber. 106, page 3,626). The carbodiimide method wherein an active ester-forming component, preferably 1-hydroxybenzotriazole, is added, is likewise preferred.

The reaction may take place in a solvent suitable for this purpose. Preferred solvents are dialkylamides such as dimethylformamide, dimethylacetamide or N-methylpyrrolidone. The concentration of the reaction partners corresponds to that usual in syntheses of this type.

The reaction takes place at a temperature at which the solvent used is present in liquid form and at which the reaction partners are not damaged in irreversible manner. The preferred reaction temperature is in the range of from about 0° to about 40°-60° C., room temperature being particularly preferred.

Suitable N-protective groups according to the present invention are all radicals that can be readily split off by proton solvolysis as well as photosensitive radicals or radicals removable by β-elimination, for example benzoxycarbonyl, tert. alkyl, tert. aralkyl and alkyloxycarbonyl; or trityl, 2-nitrophenylsulfenyl, 1-methyl-2-acyl-vinyl and trifluoroacetyl. Suitable protective groups are, finally, amino acids protected by nitrogen that can be split off by means of enzymes, for example acylarginine. These protective groups are described in detail in the above-mentioned "Publication of Houben-Weyl." The formyl radical and especially groups that have to be eliminated under conditions under which the formyl radical is also eliminated are unsuitable as N-protective groups according to the present invention. An example hereof is phthaloyl that can be split off by hydrazine, like formyl. Further, protective groups that can be split off only with bromocyanogen or with an oxidizing compound are unsuitable. The same applies to compounds of the formula I wherein X represents a sulfur-containing substituent. The tosyl radical, too, is unsuitable because it can be split off only with difficulty.

In Table 1 there are summarized some characteristic compounds according to the present invention.

TABLE 1

| | Characteristic data of the compounds according to the present invention | | | | |
|---|---|---|---|---|---|
| X | Rf[1] | F | character-ized by[2] | | $[\alpha]_D$ (C = 1, DMF) |
| Phe—NH—(CH₂)₅—CH₃ | 0.57 | | AA, | CHN | +17° |
| Phe—Pro—NH—(CH₂)₅—CH₃ | 0.53 | | AA | | −12° |
| Phe—Pro—NH₂ | 0.39 | | AA, | CHN | −20.8° |
| Nᵅ—Z—compound | | 125–7° | | CHN | |
| Phe—NH 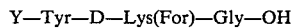 CH₃ | 0.58 | | AA, | CHN | −5.4° |
| Nᵅ—Boc-compound | | 161–2° | | CHN | |
| Phe—N  | 0.48 | | AA | | |
| Nᵅ—Boc-compound | | | | CHN | |

TABLE 1-continued

Characteristic data of the compounds according to the present invention

| X | Rf[1] | F | characterized by[2] | $[\alpha]_D$ (C = 1, DMF) |
|---|---|---|---|---|
| Phe—N⟨piperidinyl⟩ | 0.49 | | AA | +8.3° |
| $N^\alpha$—Boc-compound | | 84° | CHN | |
| Phe—N⟨azepane⟩ | 0.45 | | AA | +19.5° |
| $N^\alpha$—Boc-compound | | | CHN | |
| Phe—N⟨piperidinyl-CONH₂⟩ | 0.40 | | AA | +7.4° |
| $N^\alpha$—Boc-compound | | 112–3° | CHN | |
| Phe—NH⟨piperidinone⟩ | 0.37 | | AA | −1.1° |
| $N^\alpha$—Boc-compound | | 138° | CHN | |
| Phe—N⟨piperazine⟩—N—CH₂—CH₂—CH₃ | 0.20 | | AA | +2.6° |
| $N^\alpha$—Boc-compound | | 198–200° | CHN | |
| Phe—N⟨thiazolidine⟩ | 0.43 | | AA, CHN | +20° |
| Phe—N⟨dimethylthiazolidine⟩ | 0.51 | | AA, CHN | +25° |
| Phe—N⟨dimethylthiazolidine-COOH⟩ | 0.15 | | AA, CHN | −10.5° |
| Phe—NH⟨thiolactone⟩ | 0.45 | | AA | +7.7° |
| $N^\alpha$—Boc-compound | | 167–8° | CHN | |
| Phe—endo-norbornylamide | 0.57 | | AA | +3.4° |
| $N^\alpha$—Boc-compound | | 119° | CHN | |
| Phe—exo-norbornylamide | 0.58 | | AA | +4.8° |
| $N^\alpha$—Boc-compound | | 108° | CHN | |

TABLE 1-continued

Characteristic data of the compounds according to the present invention

| X | Rf[1] | F | characterized by[2] | $[\alpha]_D$ (C = 1, DMF) |
|---|---|---|---|---|
| Phe—NH—CH$_2$—[pyrrolidine with N—CH$_2$—CH$_3$] | 0.17 | | AA | +3.8° |
| N$^\alpha$—Boc-compound | | 86° | CHN | +10.0° |
| Phe—NH—CH(CH$_3$)—CH$_2$—OH | 0.44 | | AA | |
| N$^\alpha$—Boc-compound | | 145-8° | CHN | |
| Phe—NH—CH$_2$—CH(OH)—CH$_3$ | 0.44 | | AA | +6.1° |
| N$^\alpha$—Boc-compound | | 146° (dec.) | CHN | |
| —NH—CH(CH$_2$—OH)(CH(OH)—C$_6$H$_5$) | 0.50 | | AA | +52.6° |
| N$^\alpha$—Boc-compound | | | CHN | +28.8° |
| Phe—NH—CH(CH$_2$—OH)(CH(C$_6$H$_5$)—OH) | 0.49 | | AA | +23.5° |
| N$^\alpha$—Boc-compound | | | CHN | +12.8° |

[1]DC in system n-butanol/acetic acid/water (3:1:1) standard: Tyr—D-Lys(For)—Gly—Phe—OH:R$_f$ = 0.42
[2]AA = Amino acid analysis
CHN = elementary analysis of C, H and N The compounds according to the invention are capable of charging morphine receptors. Consequently, they act analgetically and suppress the motility of the ileum of the guinea pig.

The compounds according to the invention are effective when administered intravenously at a dose from 1 to 100 mg/kg, preferably from 1 to 10 mg/kg. When administered to dogs at a dose as small as 0.01 mg/kg, they surprisingly provoke an extreme increase of the intestinal motility. They are hence suitable for the treatment of postoperative intestinal atony. They are administered preferably in isotonic aqueous solution at pH 4–6 intravenously or intramuscularly or intranasally.

Table 2 shows the biological activity of a characteristic compound according to the invention (A), as compared to a very effective peptide derivative (B) known from Biochem.Biophys.Res.Commun. 84 (1978), page 1045: (ED+100%: doubled reaction time, ED$_{50}$: reduction of the response to excitation by 50%).

TABLE 2

Biological activity of the compounds according to the invention illustrated by the peptide derivative according to claim 3

| | Peptide derivative | Analgesia mouse ED + 100% mg/kg | Ileum of guinea pig ED$_{50}$ g/ml | Intestinal motility (dog) with 0.01 mg/kg |
|---|---|---|---|---|
| A | Tyr—D-Lys(For)—Gly—Phe—NH$_2$ | 2 | 3.10$^{-10}$ | effective |
| B | Tyr—D-Lys(For)—Gly—Phe—NH—[thiolactone ring O=C, S] | 2 | 3.10$^{-9}$ | — |

It can be seen that the activity of the compound according to the invention with regard to the ileum of the guinea pig is ten times greater than that of the comparative substance, although the analgetic activity of both compounds is equal. Hence the activity ranges of both compounds distinctly differ from one another. This is emphasized by the novel effect on the intestinal motility of the dog, even when administered in very small doses.

The following examples illustrate the synthesis of some characteristic compounds according to the invention. The other compounds according to the invention are obtainable in analogous manner:

EXAMPLE 1

L-Tyrosyl-D-N$^\epsilon$-formyllysyl-glycyl-L-phenylalanyl-homocysteine-thiolactone-trifluoroacetate (a) Benzyloxycarbonyl-glycyl-phenylalanine 16.5 g of phenylalanine are suspended in 150 ml of dimethylformamide (DMF), 13.5 g of 1-hydroxybenzotriazole, 38.8 g of benzyloxycarbonylglycine-trichlorophenyl ester and 12.8 ml of N-ethylmorpholine are added and the batch is stirred for 8 hours at room temperature. The product is concentrated in vacuo, dissolved in 1 liter of ethyl acetate and submitted to repeated extractions with 200ml portions of 2 N citric acid and of saturated sodium chloride solution, respectively. The organic phase is dried over sodium sulfate and concentrated in vacuo. The residue crystallizes from ethyl acetate/diisopropyl ether.

Yield: 23.5 g=66%.

F: 125°–126° C. $[\alpha]_D^{22}=+28.1$ (c=1, methanol).

(b) Glycyl-phenylalanine-hydrochloride 23 g of benzyloxycarbonyl-glycyl-phenylalanine are dissolved in 250 ml of a methanol/dimethylformamide mixture (1:1) and submitted to hydrogenation by adding 1 g of palladium/charcoal (5% of Pd) (Pd/C) as the catalyst. The pH is kept constant at 4.5 by adding methanolic hydrochloric acid. After removal of the catalyst, the filtrate is concentrated in vacuo and the residue is precipitated from methanol by adding ether.

Yield: 14.5 g=93%.

F: 264°–265° C. $[\alpha]_D^{22}=30.7°$ (c=1, 2N HCl).

(c) Benzyloxycarbonyl-D-N$^\epsilon$-formyllysyl-glycyl-phenylalanine 15 g of glycyl-phenylalanine-hydrochloride are suspended in 200 ml of DMF and stirred with 7.8 g of 1-hydroxybenzotriazole and 28.3 g of benzyloxycarbonyl-D-N$^\epsilon$-formyllysine-trichlorophenyl ester with the addition of 7.5 ml of N-ethylmorpholine, for 8 hours, at room temperature. The product is concentrated in vacuo, dissolved in acetic acid and extracted with 2N citric acid and NaCl solution. The organic phase is dried over sodium sulfate, somewhat concentrated and crystallized by adding ether.

Yield: 22.4 g=75%.

F: 150°–152° C. $[\alpha]_D^{22}=+7°$ (c=1, methanol).

(d) D-N$^\epsilon$Formyllysyl-glycyl-phenylalanine 22 g of benzyloxycarbonyl-D-N$^\epsilon$-formyllysyl-glycyl-phenyl-alanine are dissolved in a mixture of DMF/water (1:1), 500 mg of Pd/C are added and the product is submitted to catalytic hydrogenation. The filtrate is concentrated in vacuo and crystallized subsequently from a small quantity of aqueous methanol.

Yield: 13.2 g=81%.

F: 180°–181° C. $[\alpha]_D^{22}=-2.4$ (c=1, 2N HCl).

(e) tert. Butyloxycarbonyl-O-tert.butyl-tyrosyl-D-N$^\epsilon$-formyllysyl-glycyl-phenylalanine 13 g of D-N$^\epsilon$-formyllysyl-glycyl-phenylalanine are suspended in 250 ml of DMF and stirred subsequently with 4.6 g of 1-hydroxybenzotriazole, 14.9 g of tert. butyloxy-carbonyl-O-tert.butyl-tyrosine-N-hydroxysuccinimide ester and 4.4ml of N-ethyl-morpholine, for 24 hours, at room temperature. The product is concentrated in vacuo and subsequently dissolved in ethyl acetate. The reaction mixture dissolved in ethyl acetate is submitted to extraction with 2N citric acid and aqueous sodium chloride solution and the extract is crystallized from acetic acid/ether.

Yield: 17 g=71%.

F: 123°–124° C. $[\alpha]_D^{22}=+40.3°$ (c=1, methanol).

(f) tert.Butyloxycarbonyl-O-tert.butyl-tyrosyl-D-N$^\epsilon$-formyllysyl-glycyl-phenylalanyl-homocysteine thiolactone 3.49 g of BOC-Tyr(Bu$^t$)-D-Lys(For)-Gly-Phe-OH are dissolved in 20 ml of DMF by means of 675 mg of 1-hydroxybenzotriazole and 768 mg of DL-homocysteine-thiolactone-hydrochloride. The resulting solution is cooled to 0° C. and 640 μl of N-ethylmorpholine and 1.04 g of dicyclohexylcarbodiimide are added. After a reaction time of 2 hours at 0° C., the product is kept at room temperature for 4 hours. The precipitated dicyclohexylurea is suction-filtered and the filtrate is concentrated to dryness. The pure title compound is obtained by column chromatography on silica gel (about 600 g) using as eluant chloroform/methanol at a ratio of 5.5:1.

Yield: 3.0 g=70%.

(g) Tyrosyl-D-N$^\epsilon$-formyllysyl-glycyl-phenylalanyl-homocysteine-thiolactone-trifluoroacetate 2 g of the compound obtained according to (f) are treated with 0.2 ml of anisole and 15 ml of trifluoroacetic acid for 40 minutes at room temperature. A precipitate is obtained upon addition of 1 liter of ether and subsequently centrifuged. The substance is triturated several times with ether and the supernatant is decanted.

Yield: 1.7 g=85%.

EXAMPLE 2

L-Tyrosyl-D-N$^\epsilon$-formyllysyl-glycyl-dehydrophenylalanyl-L-prolinamide-trifluoroacetate (a) Benzyloxycarbonyl-glycyl-dehydrophenylalanyl-prolinamide 11 g of benzyloxcarbonyl-glycyl-dehydrophenylalanine-azlactone and 4.95 g of prolinamide-hydrochloride are dissolved in a sufficient quantity of DMF, 4.4 ml of N-ethylmorpholine are added and the product is left to stand at room temperature for 24 hours. The product is concentrated by evaporation and the residue is submitted to chromatography on a silica gel column (8×60cm) using as eluent CHCl$_3$/methanol at a ratio of 8:3.

Yield: 4.63 g=31%

F: 199°–200° C.

(b) Glycyl-dehydrophenylalanyl-prolinamide-hydrobromide 1.3 g of benzyloxycarbonyl-glycyl-dehydrophenylalanyl-prolinamide are dissolved in 6 ml of 30% HBr in glacial acetic acid. After a reaction time of 20 minutes, at room temperature, the product is precipitated with ether, centrifuged and washed several times with ether.

Yield: 1.14 g=97%

F: 160° C. (decomp.)

(c) N$^\alpha$-Benzyloxycarbonyl-D-N$^\epsilon$-formyllysyl-glycyl-dehydrophenylalanyl-prolinamide 1.14 g of glycyl-dehydrophenylalanyl-prolinamide-hydrobromide and 1.26 g of benzyloxycarbonyl-N$^\epsilon$-formyllysyl-trichlorophenyl ester (lysine active ester) are dissolved in the required quantity of DMF, 0.36 ml of N-ethylmorpholine and 387 mg of 1-hydroxybenzotriazole are added and the product is stirred at room temperature for 18 hours. After adding a further 140 mg of lysine active ester and after a reaction time of 6 hours, the product is evaporated, the residue is dissolved in chloroform and submitted to extraction with 2N citric acid, water and 5% KHCO$_3$ solution. The product is dried over sodium sulfate and the organic phase is concentrated to dryness.

Yield: 1.2 g=70%

F: 100° C. (decomp.)

(d) D-N$^\epsilon$-Formyllysyl-glycyl-dehydrophenylalanyl-prolinamide-hydrobromide 800 mg of the benzyloxycarbonyl compound prepared according to (d) are dissolved in 5 ml of 30% HBr in glacial acetic acid and the resulting solution is stirred for 20 minutes. The product is precipitated with ether, centrifuged and washed several times with ether.

Yield: 700 mg=96%

(e) tert.Butyloxycarbonyl-O-tert.butyl-tyrosyl-D-N$^\epsilon$-formyllysyl-glycyl-dehydrophenylalanyl-prolinamide 800 mg of D-N$^\epsilon$-formyllysyl-glycyl-dehydrophenylalanine-prolinamide-hydrobromide are dissolved in conjunction with 415 mg of tert.butyloxycarbonyl-O-tert.butyl-tyrosine, 0.18 ml of N-ethylmorpholine and 915 mg of 1-hydroxybenzotriazole in 10 ml of DMF. While cooling with ice there is added a solution of 300 mg of dicyclohexylcarbodiimide in DMF and the product is stirred for 18 hours at room temperature. The product is filtered and the filtrate is concentrated to dryness. The residue is dissolved in glacial acetic acid and submitted to extraction with 50 ml portions of 2N citric acid, water and 5% sodium bicarbonate solution, respectively. The residue of the organic phase is purified chromatographically on a 2.5×40 silica gel column using CHCl$_3$/methanol/glacial acetic acid at a ratio of 50:50:5 as the eluant.

Yield: 426 mg=43%.

(f) Tyrosyl-D-N$^\epsilon$-formyllysyl-glycyl-dehydrophenylalanyl-prolinamide-trifluoroacetate 426 mg of the BOC compound obtained according to (e) are dissolved in 50 μl of anisole and 5 ml of trifluoroacetic acid and the resulting solution is stirred at room temperature for 30 minutes. The product is precipitated with 100 ml of ether and subsequently centrifuged.

Yield: 370 mg=92%
F: 160°-165° C. $[\alpha]_D^{22}$+73.6 (c=1, methanol)
C: calc. 54.5; found: 54.2.
H: calc. 5.6; found: 5.4.
N: calc. 13.1; found: 12.8.

EXAMPLE 3

L-Tyrosyl-D-N$^\epsilon$formyllysyl-glycyl-(L-threo-1.3-dihydroxy-1-phenyl)-propane-2-amide (a) tert.Butyloxycarbonyl-glycine-(L-threo-1.3-dihydroxy-1-phenyl)-propane-2-amide 10.6 g of tert.butyloxycarbonyl-glycine-trichlorophenyl ester and 5 g of L(+)-threo-1-phenyl-2-amino-propane-1.3-diol are introduced into 40 ml of acetonitrile and briefly heated until a clear solution is obtained. This solution is left at room temperature for 14 hours, concentrated in vacuo and dissolved in ethyl acetate. The organic phase is extracted with 2N citric acid and aqueous sodium bicarbonate solution, the extract is dried over solid sodium sulfate and concentrated in vacuo, leaving a colorless oil.

$R_f$(CHCl$_3$-CH$_3$OH 8:3) 0.45 (plate material:silica gel 60)

(b) Glycine-(L-threo-1.3-dihydroxy-1-phenyl)-propane-2-amide-trifluoroacetate

The total quantity of the BOC compound obtained according to (a) is treated for 30 minutes with 30 ml of trifluoroacetic acid. The product is concentrated in vacuo and the residue is triturated with a mixture of diisopropyl ether and anhydrous petroleum ether. The highly hygroscopic substance, deliquescing on exposure to the air, is dried over KOH in vacuo and stored.

Yield: 10 g=90%

(c) tert.Butyloxycarbonyl-D-N$^\epsilon$-formyllysyl-glycine-(L-threo-1.3-dihydroxy-1-phenyl)-propane-2-amide 0.82 g of glycine-dihydroxy-phenyl-propanamide-trifluoracetate prepared according to (b) and 1.73 g of tert.butyloxycarbonyl-D-N$^\epsilon$-formyllysine-trichlorophenyl ester, to which 0.48 ml of N-ethylmorpholine and 0.5 g of 1-hydroxybenzotriazole have been added, are reacted in acetic acid/DMF (1:1). After 60 hours, the product is concentrated in vacuo leaving an oil that is chromatographied on a silica gel column (2.5×40 cm) using chloroform/methanol, with a gradient of 9:1 to 8:4 as the eluant. The fraction having the $R_f$ value mentioned below is concentrated and precipitated with ether.

Yield: 1.1 g=47%, $R_f$=0.6 (CHCl$_3$/MeOH/acetic acid 50:50:5).

(d) D-N$^\epsilon$-Formyllysyl-glycine-(L-threo-1.3-dihydroxy-1-phenyl)-propane-2-amide-trifluoroacetate 1.1 g of BOC-D-Lys(For)-Gly-NH-CH(CH$_2$OH)-CHOH-C$_6$H$_5$ obtained according to (c) are stirred in 5 ml of trifluoroacetic acid with the addition of some anisole, for 45 minutes. The product is somewhat concentrated in vacuo and precipitated with diethyl ether.

Yield: 105 g=93%
F: 98°-99°, $[\alpha]_D^{22}$=+52.6 (c=1, methanol)

(e) tert.Butyloxycarbonyl-tyrosyl-D-N$^\epsilon$-formyllysyl-glycine-(L-threo-1.3-dihydroxy-1phenyl)-propane-2-amide 1 g of D-Lys(For)-Gly-NH-CH(CH$_2$OH)-CHOH-C$_6$H$_5$·CF$_3$COOH (obtained according to (d)) and 0.93 g of tert.butyloxycarbonyl-tyrosine-trichlorophenyl ester are reacted in DMF while adding 0.26 ml of N-ethylmorpholine and 0.27 g of 1-hydroxybenzotriazole. After 60 hours the product is concentrated in vacuo, dissolved in ethyl acetate and extracted with 2N citric acid, water and a sodium bicarbonate solution.

Crude yield: 1.2 g=96%

The crude product is purified by chromatography over a silica gel column (190 g of SiO$_2$) using chloroform/methanol/glacial acetic acid at a ratio of 50:30:3 as the eluant.

Yield: 0.7 g=56%
F: 96°-97° C. (decomp.)

(f) Tyrosyl-D-N$^\epsilon$-formyllysyl-glycyl-(L-threo-1.3-dihydroxy-1-phenyl)-propane-2-amide 0.7 g of BOC-Tyr-D-Lys(For)-Gly-NH-CH(CH$_2$OH)-CHOH-C$_6$H$_5$ is stirred with 5 ml of trifluoroacetic acid/anisole (1:1) for 45 minutes. The product is a little concentrated in vacuo, precipitated by the addition of ether and washed several times with ether.

Yield: 0.5 g=70%
F: 73°-74° C. (decomp.) $[\alpha]_D^{22}$=+23.6
Amino acid analysis:
Gly 1.04; Tyr 0.96; Lys 1.00; further component 1.07 (measured as Phe).

What is claimed is:

1. A peptide amide of the formula

H—Tyr—D—Lys(For)—Gly—X, wherein For is formyl and X is alkylamido, dehydro-Phe-alkylamido, or Phe-alkylamido each having up to 6 carbon atoms in the alkyl, or is such alkylamido, dehydro-Phe-alkylamido, or Phe-alkylamido substituted in the alkyl portion thereof by at least one member selected from the group consisting of hydroxy and phenyl; Phe-cycloalkyl amido or Phe-cycloalkylene amido having up to 8 carbon atoms in the cycloalkyl or cycloalkylene, or such Phe-cycloalkyl amido or Phe-cycloalkylene amido wherein one or two —CH$_2$—groups may be replaced by one or two members selected from the group consisting of —NH—, —O—, —S—, and —CO—; Phe-alkylene-cycloalkyl amido having 5 to 6 ring carbon atoms or such Phe-alkylene-cycloalkyl amido substituted by alkyl, carbonamido, or N-alkyl-carbonamido, or wherein one carbon atom may be replaced by nitrogen; Phe-endo-norbornylamido; Phe-exo-norbornylamido; or Phe-thiazolamido or Phe-thiazolidine-carboxylic acid amido or such Phe-thiazolamido or Phe-thiazolidine-carboxylic acid amido substituted by 1 to 4 methyl groups.

2. L-Tyrosyl-D-N$^\epsilon$-formyllysyl-glycyl-L-phenylalanyl-homocysteine-thiolactone.

* * * * *

UNITED STATES PATENT AND TRADEMARK OFFICE
CERTIFICATE OF CORRECTION

PATENT NO. : 4,459,225

DATED : July 10, 1984

INVENTOR(S) : Teetz et al.

It is certified that error appears in the above-identified patent and that said Letters Patent is hereby corrected as shown below:

In Table 2, column 5, lines 60 to 65, change

"A   Tyr-D-Lys(For)-Gly-Phe-$NH_2$

B   Tyr-D-Lys(For)-Gly-Phe-NH 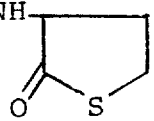  "  to

--A   Tyr-D-Lys(Fcr)-Gly-Phe-NH 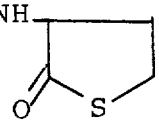

B   Tyr-D-Met-Gly-Phe-Pro-$NH_2$ --.

Signed and Sealed this

Twenty-first Day of May 1985

[SEAL]

Attest:

DONALD J. QUIGG

Attesting Officer   Acting Commissioner of Patents and Trademarks